United States Patent
Zhou

(10) Patent No.: US 9,422,216 B2
(45) Date of Patent: Aug. 23, 2016

(54) METHOD FOR SYNTHESIS OF LACTIC ACID AND ITS DERIVATIVES AND CATALYST FOR PREPARING SAME

(71) Applicant: MICROVAST POWER SYSTEMS CO., LTD., Huzhou, Zhejiang (CN)

(72) Inventor: Xiaoping Zhou, Huzhou (CN)

(73) Assignee: Microvast Power Systems Co., Ltd, Huzhou (CN)

(*) Notice: Subject to any disclaimer, the term of this patent is extended or adjusted under 35 U.S.C. 154(b) by 0 days.

(21) Appl. No.: 14/424,760

(22) PCT Filed: Aug. 27, 2013

(86) PCT No.: PCT/CN2013/082361
§ 371 (c)(1),
(2) Date: Aug. 5, 2015

(87) PCT Pub. No.: WO2014/032567
PCT Pub. Date: Mar. 6, 2014

(65) Prior Publication Data
US 2015/0329458 A1    Nov. 19, 2015

(30) Foreign Application Priority Data

Aug. 27, 2012 (CN) .......................... 2012 1 0307028

(51) Int. Cl.

| | | |
|---|---|---|
| *C07C 51/00* | (2006.01) | |
| *B01J 27/00* | (2006.01) | |
| *B01J 27/138* | (2006.01) | |
| *B01J 27/135* | (2006.01) | |
| *B01J 27/125* | (2006.01) | |
| *B01J 27/132* | (2006.01) | |
| *B01J 27/08* | (2006.01) | |
| *C01G 30/00* | (2006.01) | |
| *C01G 19/06* | (2006.01) | |
| *C01G 9/04* | (2006.01) | |
| *C01G 37/04* | (2006.01) | |
| *C01F 7/56* | (2006.01) | |
| *C01G 3/05* | (2006.01) | |
| *C01G 19/08* | (2006.01) | |
| *C01G 19/00* | (2006.01) | |
| *C01G 51/08* | (2006.01) | |
| *C07C 67/00* | (2006.01) | |

(52) U.S. Cl.
CPC .................. *C07C 51/00* (2013.01); *B01J 27/08* (2013.01); *B01J 27/125* (2013.01); *B01J 27/132* (2013.01); *B01J 27/135* (2013.01); *B01J 27/138* (2013.01); *C01F 7/56* (2013.01); *C01G 3/05* (2013.01); *C01G 9/04* (2013.01); *C01G 19/00* (2013.01); *C01G 19/06* (2013.01); *C01G 19/08* (2013.01); *C01G 30/007* (2013.01); *C01G 37/04* (2013.01); *C01G 51/085* (2013.01); *C07C 67/00* (2013.01)

(58) Field of Classification Search
CPC ................................ C07C 51/00; B01J 27/00
USPC .................. 562/515; 502/226, 227, 228, 231
See application file for complete search history.

(56) References Cited

U.S. PATENT DOCUMENTS

2005/0119448 A1    6/2005    Matsuda et al.
2013/0231497 A1    9/2013    Zhou et al.

FOREIGN PATENT DOCUMENTS

| CN | 101265180 A | 9/2008 |
| CN | 102603512 A | 7/2012 |
| EP | 2100871 A1 | 9/2009 |
| WO | WO 2012/065002 A1 | 5/2012 |

OTHER PUBLICATIONS

English Translation of CN 102603512 (Jul. 25, 2012).*
English Abstract of CN 102603512 A, Jul. 25, 2012.
Hongmei Liu, et al.; Synthesis of Ethyl Lactate Under the Condition of Microwave Irradiation 1-2 and Catalyst, Journal of Hebei Normal University of Science & Technology, Mar. 2007, vol. 21, No. 1, pp. 33-36, and the Abstract.
Youning Chen et al.; Study on technology for the synthesis of n-butyl lactate, Science & 1-2 Technology in Chemical Industry, Dec. 2008, vol. 16, No. 3, pp. 9-11, and the Abstract.
English Abstract of EP 2100871A1, Sep. 16, 2009.
English Abstract of CN 101265180A, Sep. 17, 2008.
English translation of Hong-mei Liu, et al.; Synthesis of Ethyl Lactate Under the Condition of Microwave Irradiation 1-2 and Catalyst, Journal of Hebei Normal University of Science & Technology, Mar. 2007, vol. 21, No. 1, 7 pages.
English translation of You-ning Chen et al.; Study on technology for the synthesis of n-butyl lactate, Science & 1-2 Technology in Chemical Industry, Dec. 2008, vol. 16, No. 3, 5 pages.

* cited by examiner

*Primary Examiner* — Sikarl Witherspoon
(74) *Attorney, Agent, or Firm* — Ladas & Parry LLP

(57) ABSTRACT

The present disclosure provides a catalyst for preparing lactic acid and derivatives thereof, comprising at least one of metallic compounds $MX_n$, wherein M is selected from Na, K, Mg, Ca, Sr, Ba, Al, Ga, In, Sn, Sb, Bi, Cr, Mn, Fe, Co, Ni and Zn, and n is an integer of 1 to 6. The present disclosure further provides a method for synthesis of lactic acid and derivatives thereof, wherein at least one raw material including carbohydrates, at least one alcohol, at least one of the aforesaid catalysts and at least one solvent are heated to react to prepare lactic acid and derivatives thereof.

22 Claims, 2 Drawing Sheets

METHOD FOR SYNTHESIS OF LACTIC ACID AND ITS DERIVATIVES AND CATALYST FOR PREPARING SAME

RELATED APPLICATIONS

This application is a national phase entry under 35 U.S.C. 371 of International Patent Application No. PCT/CN2013/082361 filed on 27 Aug. 2013, which claims priority from Chinese Patent Application No. 201210307028.0 filed on 27 Aug. 2012, the disclosures of which are incorporated in their entirety by reference herein.

FIELD OF THE INVENTION

The present disclosure relates to a catalyst for preparing lactic acid and derivatives thereof, and a method for synthesis of lactic acid and derivatives thereof with the catalyst.

BACKGROUND OF THE INVENTION

Glucose, sucrose, starch and cellulose are the most abundant renewable sources found in the earth for carbohydrates. These carbohydrates have high contents of oxidation groups, so it is very favorable to manufacture basic chemicals with them. Especially, without releasing carbon dioxide, these carbohydrates are the most attractive raw materials for synthesis of chemical intermediates in a sustainable manner.

Theoretically, each mole of hexose could be converted into two moles of lactic acid through fermentation or catalytic reaction. Lactic acid is a monomer for synthesis of biodegradable polylactic acids. Lactic acid and derivatives thereof (such as alkyl lactates and polylactic acids) may be used for synthesis of other three-carbon compounds such as propylene glycol, acrylic acid and allyl alcohol, and these three-carbon compounds may be used for synthesis of other polymers.

In the current chemical industry, lactic acid is produced by fermentation of glucose, referring to FIG. 1. However, the fermentation process only provides a very dilute lactic acid fermentation broth (<10% aqueous solution) which may react with calcium hydroxide to afford solid calcium lactate which then reacts with a sulfuric acid solution to afford lactic acid. The fermentation process will produce massive wastewater and solid calcium sulfate waste, and the fermentation process of lactic acid only uses glucose as the raw material. Existing fermentation processes can produce lactic acid in a large scale (120,000 tons/year) with glucose. However, the problem with microbial fermentation is that the reaction rate is low and the concentration of the product is low (in water), so the reaction time is long, reactors with large volumes are required, and the energy consumption during product purification is high (please refer to Fermentation of Glucose to Lactic Acid Coupled with Reactive Extraction: Kailas L. Wasewar, Archis A. Yawalkar, Jacob A. Moulijn and Vishwas G. Pangarkar, Ind. Eng. Chem. Res. 2004, 43, 5969-5982).

As is well known in the art, in the presence of alkali metal hydroxides, monosaccharides could be converted into lactic acid (please refer to R. Montgomery. Ind. Eng. Chem, 1953, 45, 1144; B. Y. Yang and R. Montgomery, Carbohydr. Res. 1996, 280, 47). However, stoichiometric alkali ($Ca(OH)_2$) and acid ($H_2SO_4$) will be consumed in the recovery process of lactic acid. Thus, corresponding stoichiometric salt waste is produced.

The commercial fermentation process can produce massive lactic acid, but it only uses starch as the raw material, and starch must be pre-hydrolyzed (or fermented) so as to afford glucose. The fermentation process produces massive wastewater and solid waste ($CaSO_4$). Moreover, the fermentation process for producing lactic acid includes many steps and requires consuming considerable energy. The essential equipments required by the fermentation process are very complicated and not economical.

SUMMARY OF THE INVENTION

The present disclosure provides an economical method for preparing lactic acid and derivatives thereof directly from carbohydrate raw materials through a non-fermentation process.

The present disclosure provides a catalyst for preparing lactic acid and derivatives thereof, and the aforesaid catalyst comprises at least one of metallic compounds $MX_n$, wherein M is selected from Li, Na, K, Mg, Ca, Sr, Ba, Al, Ga, In, Sn, Sb, Bi, Cr, Mn, Fe, Co, Ni and Zn, and n is an integer of 1 to 6; the anion X of the aforesaid metallic compound $MX_n$ is selected from $F^-$, $Cl^-$, $Br^-$, $I^-$, $SO_4^{2-}$, $HSO_4^-$, $CH_3SO_3^-$, $C_6HSO_3^-$, $H_2PO_4^-$, $HPO_4^{2-}$, $PO_4^{3-}$, $PF_6^-$, $BO_4^-$, $BF_4^-$, $SiF_6^{2-}$ and $CH_3CO_2^-$.

According to an embodiment of the present disclosure, the metal cation M of the aforesaid metallic compound $MX_n$ is selected from $Li^+$, $Na^+$, $K^+$, $Mg^{2+}$, $Ca^{2+}$, $Sr^{2+}$, $Ba^{2+}$, $Al^{3+}$, $Ga^{3+}$, $In^{3+}$, $Sn^{2+}$, $Sn^{4+}$, $Sb^{3+}$, $Bi^{3+}$, $Cr^{3+}$, $Cr^{6+}$, $Mn^{2+}$, $Fe^{2+}$, $Fe^{3+}$, $Co^{2+}$, $Ni^{2+}$ and $Zn^{2+}$.

According to an embodiment of the present disclosure, the anion of the aforesaid metallic compound $MX_n$ is preferably selected from $F^-$, $Cl^-$, $Br^-$, $I^-$, $SO_4^{2-}$, $HSO_4^-$, $CH_3SO_3^-$, $C_6H_5SO_3^-$ and $CH_3CO_2^-$.

According to an embodiment of the present disclosure, the aforesaid catalyst for preparing lactic acid and derivatives thereof comprises at least one metal halide.

According to an embodiment of the present disclosure, the aforesaid catalyst for preparing lactic acid and derivatives thereof comprises at least one metal chloride.

According to an embodiment of the present disclosure, the aforesaid metal chloride is any one of $SbCl_3$, $SnCl_2$, $SnCl_4$, $ZnCl_2$, $CrCl_6$, $AlCl_3$, $CuCl_2$, $CoCl_2$, $BaCl_2$ and $FeCl_3$.

According to an embodiment of the present disclosure, the catalyst for preparing lactic acid and derivatives thereof may be further selected from any one of $SnSO_4$, $(CH_3SO_3)_2Sn$ and $SnC_2O_4$.

According to an embodiment of the present disclosure, the catalyst for preparing lactic acid and derivatives thereof comprises at least two of the metallic compounds $MX_n$, at least one of which is a metal halide.

According to an embodiment of the present disclosure, the catalyst for preparing lactic acid and derivatives thereof comprises at least two of the metallic compounds $MX_n$, at least one of which is a metal chloride.

According to an embodiment of the present disclosure, the catalyst for preparing lactic acid and derivatives thereof comprises at least two of the metallic compounds $MX_n$, at least one of which is a metal chloride which is $SnCl_2$, $SnCl_4$ or $SbCl_3$.

According to an embodiment of the present disclosure, the catalyst for preparing lactic acid and derivatives thereof is selected from any one of combinations of $SnCl_2$ and $MgCl_2$, combinations of $SnCl_2$ and $NaCl$, combinations of $SnCl_2$ and $CaCl_2$, combinations of $SnCl_2$ and $AlCl_3$, combinations of $SnCl_2$ and $FeCl_3$, combinations of $SnCl_2$ and $SbCl_3$, combinations of $SnCl_2$ and $ZnCl_2$, and combinations of $SnCl_2$ and $ZnBr_2$.

According to an embodiment of the present disclosure, the catalyst for preparing lactic acid and derivatives thereof may be selected from any one of combinations of $SbCl_3$ and $CrCl_3$, combinations of SbCl$_3$ and NaCl, combinations of SbCl$_3$ and CaCl$_2$, combinations of SbCl$_1$ and AlCl$_3$, combinations of SbCl$_3$ and FeCl$_3$, combinations of SbCl$_3$ and ZnCl$_2$, and combinations of SbCl$_3$ and ZnBr$_2$.

The present disclosure further provides a method for synthesis of lactic acid and derivatives thereof, wherein at least one raw material comprising carbohydrates, at least one alcohol, at least one catalyst and at least one solvent are heated to react to prepare lactic acid and derivatives thereof; the aforesaid catalyst comprises at least one of metallic compounds MX$_n$, wherein M is selected from Li, Na, K, Mg, Ca, Sr, Ba, Al, Ga, In, Sn, Sb, Bi, Cr, Mn, Fe, Co, Ni and Zn, and n is an integer of 1 to 6; the anion of the aforesaid metallic compound MX$_n$ is selected from F$^-$, Cl$^-$, Br$^-$, I$^-$, SO$_4^{2-}$, HSO$_4^-$, CH$_3$SO$_3^-$, C$_6$H$_5$SO$_3^-$, H$_2$PO$_4^-$, HPO$_4^{2-}$, PO$_4^{3-}$, PF$_6^-$, BO$_2^-$, BF$_4^-$, SiF$_6^{2-}$ and CH$_3$CO$_2^-$.

According to an embodiment of the present disclosure, the metal cation of the aforesaid metallic compound MX$_n$ is selected from Li$^+$, Na$^+$, K$^+$, Mg$^{2+}$, Ca$^{2+}$, Sr$^{2+}$, Ba$^{2+}$, Al$^{3+}$, Ga$^{3+}$, In$^{3+}$, Sn$^{2+}$, Sn$^{4+}$, Sb$^{3+}$, Bi$^{3+}$, Cr$^{3+}$, Cr$^{6+}$, Mn$^{2+}$, Fe$^{2+}$, Fe$^{3+}$, Co$^{2+}$, Ni$^{2+}$ and Zn$^{2+}$. The anion of the aforesaid metallic compound MX$_n$ is preferably selected from F$^-$, Cl$^-$, Br$^-$, I$^-$, SO$_4^{-2}$, HSO$_4^-$, CH$_3$SO$_3^-$, C$_6$H$_5$SO$_3^-$ and CH$_3$CO$_2^-$.

According to an embodiment of the present disclosure, the aforesaid catalyst comprises at least one of MX$_n$.

According to an embodiment of the present disclosure, the catalyst in the method for synthesis of lactic acid and derivatives thereof comprises at least one metal halide.

According to an embodiment of the present disclosure, the catalyst in the method for synthesis of lactic acid and derivatives thereof comprises at least one metal chloride.

According to an embodiment of the present disclosure, the aforesaid metal chloride is any one of SbCl$_3$, SnCl$_2$, SnCl$_4$, ZnCl$_2$, CrCl$_6$, AlCl$_3$, CuCl$_2$, CoCl$_2$, BaCl$_2$ and FeCl$_3$.

According to an embodiment of the present disclosure, the catalyst in the method for synthesis of lactic acid and derivatives thereof may be further selected from any one of SnSO$_4$, (CH$_3$SO$_3$)$_2$Sn and SnC$_2$O$_4$.

According to an embodiment of the present disclosure, the catalyst in the method for synthesis of lactic acid and derivatives thereof comprises at least two of the metallic compounds MX$_n$, at least one of which is a metal halide.

According to an embodiment of the present disclosure, the catalyst in the method for synthesis of lactic acid and derivatives thereof comprises at least two of the metallic compounds MX$_n$, at least one of which is a metal chloride.

According to an embodiment of the present disclosure, the catalyst in the method for synthesis of lactic acid and derivatives thereof comprises at least two of the metallic compounds MX$_n$, at least one of which is a metal chloride which is SnCl$_2$, SnCl$_4$ or SbCl$_3$.

According to an embodiment of the present disclosure, the catalyst in the method for synthesis of lactic acid and derivatives thereof may be selected from any one of combinations of SnCl$_2$ and MgCl$_2$, combinations of SnCl$_2$ and NaCl, combinations of SnCl$_2$ and CaCl$_2$, combinations of SnCl$_2$ and AlCl$_3$, combinations of SnCl$_2$ and FeCl$_3$, combinations of SnCl$_2$ and SbCl$_3$, combinations of SnCl$_2$ and ZnCl$_2$, and combinations of SnCl$_2$ and ZnBr$_2$.

According to an embodiment of the present disclosure, the catalyst in the method for synthesis of lactic acid and derivatives thereof may be selected from any one of combinations of SbCl$_3$ and CrCl$_3$, combinations of SbCl$_3$ and NaCl, combinations of SbCl$_3$ and CaCl$_2$, combinations of SbCl$_3$ and AlCl$_3$, combinations of SbCl$_3$ and FeCl$_3$, combinations of SbCl$_3$ and ZnCl$_2$, and combinations of SbCl$_3$ and ZnBr$_2$.

In the synthesis process of lactic acid and derivatives thereof, the usage amount of the catalyst needs to be adjusted based on the types of the selected catalyst; meanwhile, the types of the lactic acid derivatives resulting from different catalysts are varied; and the catalysts have different selectivity to the product, so the ratios between lactic acid and derivatives thereof from the reaction are different.

According to an embodiment of the present disclosure, the catalyst for preparing lactic acid and derivatives thereof comprises at least two of the metallic compounds MX$_n$, the ratio between the two MX$_n$ compounds needs to be adjusted based on the raw material comprising carbohydrates and the reaction conditions so as to optimize the ratio scope of the two MX$_n$ compounds.

According to an embodiment of the present disclosure, the raw material comprising carbohydrates is selected from at least one of monosaccharides and polysaccharides.

According to an embodiment of the present disclosure, the raw material comprising carbohydrates is selected from at least one of starch, glucan, sucrose, fructose and glucose.

According to an embodiment of the present disclosure, the raw material comprising carbohydrates is selected from at least one of lignocelluloses.

According to an embodiment of the present disclosure, the raw material comprising carbohydrates is selected from at least one of cotton, bagasse, corn cob, cottonseed shell, wheat straw, rice straw, and microcrystalline cellulose.

All carbohydrates that can be obtained by fermentation, hydrolysis or alcoholysis could be used as the reactants of the present disclosure.

In the case of using bagasse or cotton as the raw materials, these substances contain lignocellulose and lignin, wherein lignocellulose is the active raw material participating in the reaction, lignin cannot participate in the reaction, and due to the presence of lignin, lignocellulose in these substances cannot be fully utilized in the primary reaction. Thus, the residual raw material after the primary reaction may further be used as raw material after it is subjected to some treatments such as pulverization and ball-milling. Even if bagasse or cotton are pulverized first prior to the reaction and then used, the reaction residue after the primary reaction may still be further treated and then used as the raw material again.

The products lactic acid and derivatives thereof of the present disclosure mainly include lactic acid and/or lactate, wherein the lactate is mainly methyl lactate. The products of the present disclosure may further include byproducts such as methyl levulinate, methyl formate, and methyl acetate. The types of the products of the present disclosure are related to the adopted carbohydrate raw material, the catalyst and the reaction conditions.

In an embodiment of the present disclosure, the raw material comprising carbohydrates is bagasse, the catalyst comprises combinations of SbCl$_3$ and ZnCl$_2$, and the products of the reaction are mainly methyl lactate and methyl levulinate.

In an embodiment of the present disclosure, the raw material comprising carbohydrates is microcrystalline cellulose, the catalyst comprises combinations of SnCl$_2$ and ZnBr$_2$, and the products of the reaction are mainly methyl lactate, methyl levulinate, methyl formate and methyl acetate.

In an embodiment of the present disclosure, the raw material comprising carbohydrates is sucrose, the catalyst comprises combinations of SnCl$_2$ and MgCl$_2$, and the products of the reaction are mainly lactic acid and methyl lactate.

The aforesaid alcohol is selected from at least one of monohydric alcohols, dihydric alcohols and polyhydric alcohols. Further, the monohydric alcohol is selected from at least one of methanol, ethanol, 1-propanol, 2-propanol, 1-butanol, 2-butanol, and tert-butanol. The dihydric alcohol is selected from at least one of ethylene glycol, 1,2-propylene glycol, and 1,3-propylene glycol. The polyhydric alcohol is selected from glycerol.

In the present disclosure, the aforesaid solvent is a polar solvent which is selected from at least one of water, alcohols, and fatty acid methyl esters of C8-C22. The aforesaid solvent is required to be capable of dissolving the catalyst to form a homogenous catalyst solution.

Further, the aforesaid solvent is selected from at least one of methanol, ethanol, 1-propanol, 2-propanol, 1-butanol, 2-butanol, tert-butanol, ethylene glycol, 1,2-propylene glycol, 1,3-propylene glycol, and glycerol.

Theoretically, the mass of the alcohol in the reaction may be infinite so as to provide more chance of contact for the catalyst and the raw material to increase reaction rate, but an appropriate amount of alcohol is more economical. According to an embodiment of the present disclosure, the mass ratio of the alcohol to the carbohydrate in the raw material comprising carbohydrates is 0.5-20, and further, the mass ratio of the alcohol to the carbohydrate in the raw material comprising carbohydrates is 1-10. In an embodiment of the present disclosure, the mass ratio of the alcohol to the carbohydrate in the raw material comprising carbohydrates is 1.5.

According to an embodiment of the present disclosure, the reaction temperature for preparation of lactic acid and derivatives thereof from the raw material comprising carbohydrates is 50-300° C. Preferably, the reaction temperature for preparation of lactic acid and derivatives thereof from the raw material comprising carbohydrates is 80-220° C.

In an embodiment of the present disclosure, the raw material comprising carbohydrates is cellulose, the reaction temperature for preparation of lactic acid and derivatives thereof is 80-180° C.; and further, the reaction temperature is 100-180° C.

In an embodiment of the present disclosure, the raw material comprising carbohydrates is starch, the reaction temperature for preparation of lactic acid and derivatives thereof is 80-180° C.; and further, the reaction temperature is 80-160° C.

In an embodiment of the present disclosure, the raw material comprising carbohydrates is sucrose, the reaction temperature for preparation of lactic acid and derivatives thereof is 50-180° C.; and further, the reaction temperature is 50-140° C.

In an embodiment of the present disclosure, the raw material comprising carbohydrates is glucose, the reaction temperature for preparation of lactic acid and derivatives thereof is 50-180° C.; and further, the reaction temperature is 50-140° C.

The method provided by the present disclosure for preparing lactic acid and derivatives thereof adopts a non-fermentation process to treat the raw material comprising carbohydrates to afford lactic acid and/or lactate. This method produces less wastewater and solid waste and is environmentally friendly. Further, it features a high utilization rate of the raw material comprising carbohydrates, a simple process, and low energy consumption so that it is an economical and highly efficient method.

DETAILED DESCRIPTION OF THE INVENTION

The embodiments below describe the present disclosure in detail, but the present disclosure is not limited thereto.

Figure 1:
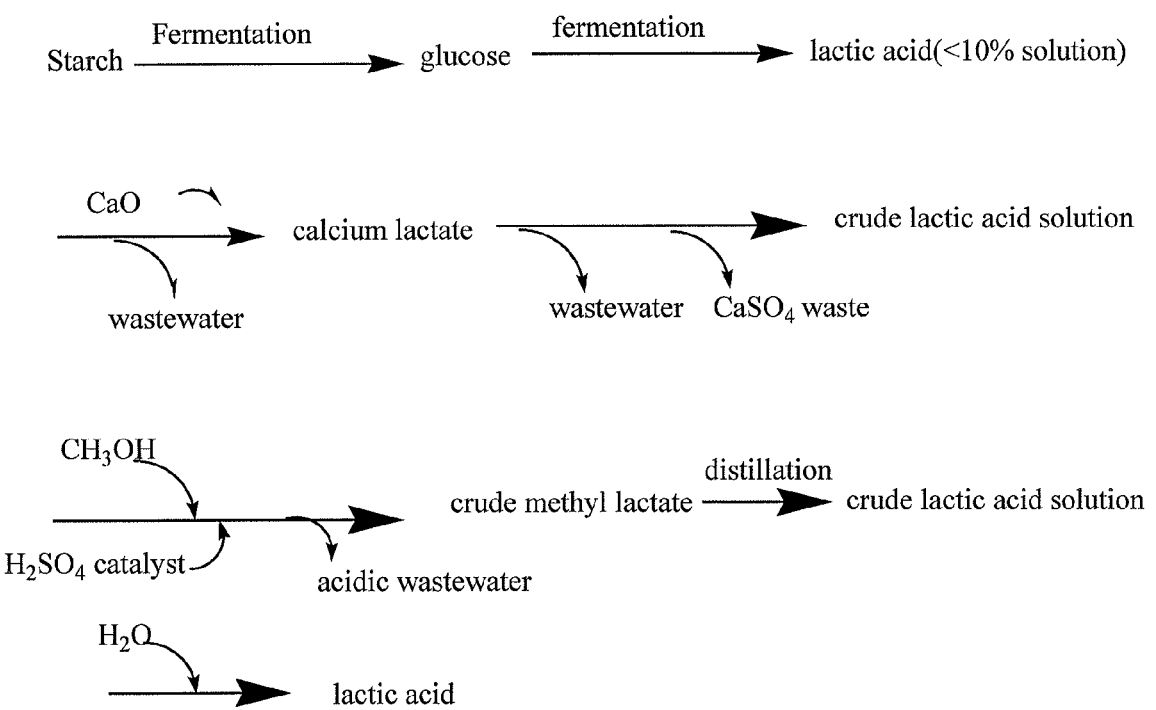
FIG. 1 is a process of the prior art for preparing lactic acid and derivatives thereof.
Figure 2:
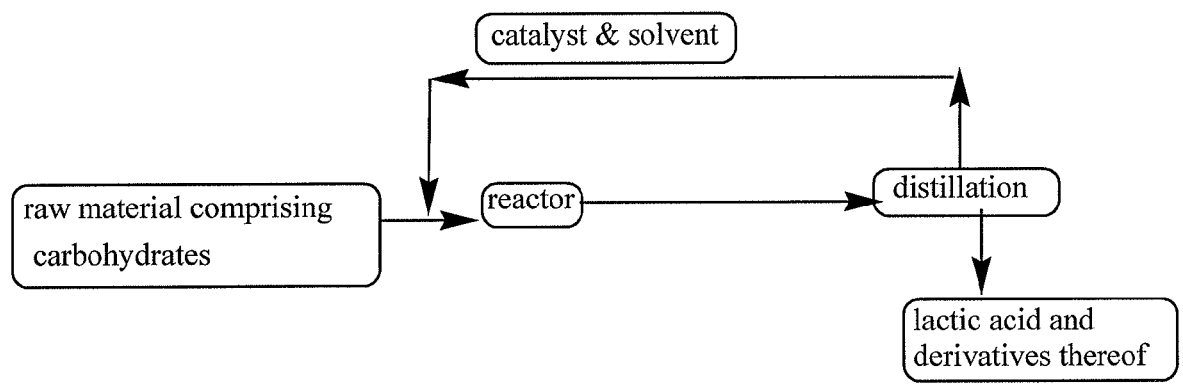
FIG. 2 is a process of one embodiment for preparing lactic acid and derivatives thereof from a raw material comprising carbohydrates.

Specifically, for the process of the present disclosure for preparing lactic acid and derivatives thereof from a raw material comprising carbohydrates, please refer to FIG. 2.

The specific examples are as follows:

EXAMPLE 1

0.2281 g of $SbCl_3 \cdot 2H_2O$, 8.010 g of methanol, and 0.4010 g of microcrystalline cellulose are added into a reactor to form a mixture. The reactor is then sealed, and heated to 180° C. with stirring to allow the mixture to react at 180° C. for 4 h. The reactor is cooled with water to room temperature. A certain quantity of n-butanol as an internal standard substance is added into the mixture, and the resulting mixture is shaken up and then taken into a centrifuge tube for centrifugal separation. Then, the supernatant is taken for gas chromatographic analysis. The yield of methyl lactate is 6.0%, the yield of methyl levulinate is 6.2%, and the yield of methyl formate is 1.1%.

EXAMPLE 2

0.2001 g of $SnCl_2 \cdot 2H_2O$, 4.000 g of methanol, and 0.2004 g of microcrystalline cellulose are added into a reactor to form a mixture. The reactor is then sealed, and heated to 180° C. with stirring to allow the mixture to react at 180° C. for 4 h. The reactor is cooled with water to room temperature. A certain quantity of n-butanol as an internal standard substance is added into the mixture, and the resulting mixture is well shaken and then taken into a centrifuge tube for centrifugal separation. Then, the supernatant is taken for gas chromatographic analysis. The yield of methyl lactate is 10.8%, the yield of methyl levulinate is 4.2%, and the yield of methyl formate is 0.2%.

EXAMPLE 3

0.3106 g of $SnCl_4 \cdot 5H_2O$, 4.000 g of methanol, and 0.2003 g of microcrystalline cellulose are added into a reactor to form a mixture. The reactor is then sealed, and heated to 180° C. with stirring to allow the mixture to react at 180° C. for 4 h. The reactor is cooled with water to room temperature. A certain quantity of n-butanol as an internal standard substance is added into the mixture, and the resulting mixture is well shaken and then taken into a centrifuge tube for centrifugal separation. Then, the supernatant is taken for gas chromatographic analysis. The yield of methyl lactate is 8.3%, and the yield of methyl levulinate is 3.7%.

EXAMPLE 4

0.1903 g of $SnSO_4$, 4.000 g of methanol, and 0.2008 g of microcrystalline cellulose are added into a reactor to form a mixture. The reactor is then sealed and heated to 180° C. with stirring to allow the mixture to react at 180° C. for 4 h. The reactor is cooled with water to room temperature, a certain quantity of n-butanol as an internal standard substance is added into the mixture, and the resulting mixture is well shaken and then taken into a centrifuge tube for centrifugal separation. Then, the supernatant is taken for gas chromatographic analysis. The yield of methyl lactate is 3.6%, and the yield of methyl levulinate is 15.9%.

EXAMPLE 5

0.2734 g of $(CH_3SO_3)_2Sn$, 4.000 g of methanol, and 0.2003 g of microcrystalline cellulose are added into a reactor to form a mixture. The reactor is then sealed, and heated to 180° C. with stirring to allow the mixture to react at 180° C. for 4 h. The reactor is cooled with water to room temperature, a certain quantity of n-butanol as an internal standard substance is added into the mixture, and the resulting mixture is well shaken and then taken into a centrifuge tube for centrifugal separation. Then, the supernatant is taken for gas chromatographic analysis. The yield of methyl lactate is 2.5%, and the yield of methyl levulinate is 11.2%.

EXAMPLE 6

0.1832 g of $SnC_2O_4$, 4.000 g of methanol, and 0.2005 g of microcrystalline cellulose are added into a reactor to form a mixture. The reactor is then sealed, and heated to 180° C. with stirring to allow the mixture to react at 180° C. for 4 h. The reactor is cooled with water to room temperature, a certain quantity of n-butanol as an internal standard substance is added into the reaction mixture, and the resulting mixture is well shaken and then taken into a centrifuge tube for centrifugal separation. Then, the supernatant is taken for gas chromatographic analysis. The yield of methyl lactate is 0.2%, and the yield of methyl levulinate is 0.3%.

EXAMPLE 7

0.1360 g of $ZnCl_2$, 8.000 g of methanol, and 0.4000 g of bagasse are added into a reactor to form a mixture. The reactor is then sealed, and heated to 190° C. with stirring to allow the mixture to react at 190° C. for 6 h. The reactor is cooled with water to room temperature, a certain quantity of n-butanol as an internal standard substance is added into the reaction mixture, and the resulting mixture is well shaken and then taken into a centrifuge tube for centrifugal separation. Then, the supernatant is taken for gas chromatographic analysis. The yield of methyl lactate is 2.0%, and the yield of methyl levulinate is 1.2%.

EXAMPLE 8

0.2369 g of $CrCl_6.6H_2O$, 8.000 g of methanol, and 0.4000 g of microcrystalline cellulose are added into a reactor to form a mixture. The reactor is then sealed, and heated to 180° C. with stirring to allow the mixture to react at 180° C. for 4 h. The reactor is cooled with water to room temperature, a certain quantity of n-butanol as an internal standard substance is added into the reaction mixture, and the resulting mixture is well shaken and then taken into a centrifuge tube for centrifugal separation. Then, the supernatant is taken for gas chromatographic analysis. The yield of methyl lactate is 4.4%, and the yield of methyl levulinate is 7.0%.

EXAMPLE 9

0.2138 g of $AlCl_3.6H_2O$, 4.000 g of methanol, and 0.2005 g of microcrystalline cellulose are added into a reactor to form a mixture. The reactor is then sealed, and heated to 180° C. with stirring to allow the mixture to react at 180° C. for 4 h. The reactor is cooled with water to room temperature, a certain quantity of n-butanol as an internal standard substance is added into the reaction mixture, and the resulting mixture is well shaken and then taken into a centrifuge tube for centrifugal separation. Then, the supernatant is taken for gas chromatographic analysis. The yield of methyl lactate is 4.3%, and the yield of methyl levulinate is 6.6%.

EXAMPLe 10

0.1511 g of $CuCl_2.2H_2O$, 4.000 g of methanol, and 0.2008 g of microcrystalline cellulose are added into a reactor to form a mixture. The reactor is then sealed, and heated to 180° C. with stirring to allow the mixture to react at 180° C. for 4 h. The reactor is cooled with water to room temperature, a certain quantity of n-butanol as an internal standard substance is added into the reaction mixture, and the resulting mixture is well shaken and then taken into a centrifuge tube for centrifugal separation. Then, the supernatant is taken for gas chromatographic analysis. The yield of methyl lactate is 3.0%.

EXAMPLE11

0.2018 g of $CoCl_2.6H_2O$, 4.000 g of methanol, and 0.2008 g of microcrystalline cellulose are added into a reactor to form a mixture. The reactor is then sealed, and heated to 180° C. with stirring to allow the mixture to react at 180° C. for 4 h. The reactor is cooled with water to room temperature, a certain quantity of n-butanol as an internal standard substance is added into the reaction mixture, and the resulting mixture is well shaken and then taken into a centrifuge tube for centrifugal separation. Then, the supernatant is taken for gas chromatographic analysis. The yield of methyl lactate is 2.3%.

EXAMPLE 12

100.0 g of $SnCl_2.2H_2O$ and 163.0 g of $MgCl_2.6H_2O$ are added into a 10.0 L reactor to act as the catalyst; next, 3.050 kg of methanol is added thereto, and then the reactor is sealed, and heated to 130° C. with stirring. 511.0 g of water and 500.0 g of sucrose are mixed to obtain a sucrose solution. The sucrose solution is then pumped into the reactor in a flow rate of 8.0 mL/min to obtain a mixture. After the sucrose solution is completely pumped into the reactor, the mixture is allowed to react at 130° C. for 1.5 h to complete the reaction. The resulting products are analyzed by GC-TCD and HPLC. The yield of methyl lactate is 53%, and the yield of lactic acid is 33%.

EXAMPLE 13

100.0 g of $SnCl_2.2H_2O$ and 163.0 g of $MgCl_2.6H_2O$ are added into a 10.0 L reactor to act as the catalyst; next, 3.005 kg of methanol is added thereto, and then the reactor is sealed, and heated to 120° C. with stirring. 511.0 g of water and 500.0 g of sucrose are mixed to obtain a sucrose solution. The sucrose solution is then pumped into the reactor in a flow rate of 8.0 mL % min to obtain a mixture. After the sucrose solution is completely pumped into the reactor, the mixture is allowed to react at 120° C. for 1.5 h to complete the reaction. The resulting products are analyzed by GC-TCD and HPLC. The yield of methyl lactate is 51%, and the yield of lactic acid is 39%.

EXAMPLE 14

100.7 g of $SnCl_2.2H_2O$ and 162.8 g of $MgCl_2.6H_2O$ are added into a 10.0 L reactor to act as the catalyst; next, 2.998 kg of methanol is added thereto, and then the reactor is sealed, and heated to 130° C. with stirring. 500.0 g of water and 500.0 g of sucrose are mixed to obtain a sucrose solution. The sucrose solution is then pumped into the reactor in a flow rate of 8.0 mL/min to obtain a mixture. After the sucrose solution is completely pumped into the reactor, the mixture is allowed to react at 130° C. for 0.5 h to complete the reaction. The resulting products are analyzed by GC-TCD and HPLC. The yield of methyl lactate is 57%, and the yield of lactic acid is 29%.

EXAMPLE 15

100.0 g of $SnCl_2.2H_2O$ and 163.0 g of $MgCl_2.6H_2O$ are added into a 10.0 L reactor to act as the catalyst; next, 2.998 kg of methanol is added thereto, and then the reactor is sealed, and heated to 130° C. with stirring. 500.0 g of water and 500.0 g of glucose are mixed to obtain a glucose solution. The glucose solution is then pumped into the reactor in a flow rate of 8.0 mL/min to obtain a mixture. After the glucose solution is completely pumped into the reactor, the mixture is allowed to react at 130° C. for 1.5 h to complete the reaction. The resulting products are analyzed by GC-TCD and HPLC. The yield of methyl lactate is 43%, and the yield of lactic acid is 31%.

EXAMPLE 16

100.0 g of $SnCl_2.2H_2O$ and 93.5 g of NaCl are added into a 10.0 L reactor to act as the catalyst; next, 3.021 kg of methanol is added thereto, and then the reactor is sealed, and heated to 130° C. with stirring. 501.5 g of water and 500.0 g of sucrose are mixed to obtain a sucrose solution. The sucrose solution is then pumped into the reactor in a flow rate of 8.0 mL/min to obtain a mixture. After the sucrose solution is completely pumped into the reactor, the mixture is allowed to react at 130° C. for 1.5 h to complete the reaction. The resulting products are analyzed by GC-TCD and HPLC. The yield of methyl lactate is 48%, and the yield of lactic acid is 28%.

EXAMPLE 17

100.0 g of $SnCl_2.2H_2O$ and 93.6 g of NaCl are added into a 10.0 L reactor to act as the catalyst; next, 3.046 kg of methanol is added thereto, and then the reactor is sealed, and heated to 130° C. with stirring. 502.4 g of water and 500.0 g of glucose are mixed to obtain a glucose solution. The glucose solution is then pumped into the reactor in a flow rate of 8.0 mL/min to obtain a mixture. After the glucose solution is completely pumped into the reactor, the mixture is allowed to react at 130° C. for 1.5 h to complete the reaction. The resulting products are analyzed by GC-TCD and HPLC. The yield of methyl lactate is 42%, and the yield of lactic acid is 33%.

EXAMPLE 18

100.0 g of $SnCl_2.2H_2O$ and 88.8 g of NaCl are added into a 10.0 L reactor to act as the catalyst; next, 3.004 kg of methanol is added thereto, and then the reactor is sealed, and heated to 130° C. with stirring. 500.0 g of water and 500.0 g of sucrose are mixed to obtain a sucrose solution. The sucrose solution is then pumped into the reactor in a flow rate of 8.0 mL/min to obtain a mixture. After the sucrose solution is completely pumped into the reactor, the mixture is allowed to react at 130° C. for 1.5 h to complete the reaction. The resulting products are analyzed by GC-TCD and HPLC. The yield of methyl lactate is 40%, and the yield of lactic acid is 26%.

EXAMPLE 19

100.0 g of $SnCl_2.2H_2O$ and 88.8 g of $CaCl_2$ are added into a 10.0 L reactor to act as the catalyst; next, 3.000 kg of methanol is added thereto, and then the reactor is sealed, and heated to 130° C. with stirring. 510.0 g of water and 500.0 g of glucose are mixed to obtain glucose a solution. The glucose solution is then pumped into the reactor in a flow rate of 8.0 ml/min to obtain a mixture. After the glucose solution is completely pumped into the reactor, the mixture is allowed to react at 130° C. for 1.5 h to complete the reaction. The resulting products are analyzed by GC-TCD and HPLC. The yield of methyl lactate is 37%, and the yield of lactic acid is 25%.

EXAMPLE 20

0.1 g of $SnCl_2.2H_2O$ and 0.5 g of $MgCl_2$ are added into a 12.0 mL reactor to act as the catalyst; next, 4.8 g of methanol, 0.2 g of water and 1.2 g of sucrose are added into the reactor to form a mixture, and then the reactor is sealed, and heated to 70° C. with stirring to allow the mixture to react for 4 h. The resulting products are analyzed by GC-TCD and HPLC. The yield of methyl lactate is 13%, and the yield of lactic acid is not analyzed.

EXAMPLE 21

0.1 g of $SnCl_2.2H_2O$ and 0.5 g of $MgCl_2$ are added into a 12.0 mL reactor to act as the catalyst; next, 4.8 g of methanol, 0.2 g of water and 1.2 g of sucrose are added into the reactor to form a mixture, and then the reactor is sealed, and heated to 80° C. with stirring to allow the mixture to react for 4 h. The resulting products are analyzed by GC-TCD and HPLC. The yield of methyl lactate is 20%, and the yield of lactic acid is not analyzed.

EXAMPLE 22

0.1 g of $SnCl_2.2H_2O$ and 0.5 g of $MgCl_2$ are added into a 12.0 mL reactor to act as the catalyst; next, 4.8 g of methanol, 0.2 g of water and 1.2 g of sucrose are added into the reactor to form a mixture, and then the reactor is sealed, and heated to 100° C. with stirring to allow the mixture to react for 4 h. The resulting products are analyzed by GC-TCD and HPLC. The yield of methyl lactate is 28%, and the yield of lactic acid is not analyzed.

EXAMPLES 23-27

A certain amount of a combination catalyst of $SnCl_2.2H_2O$ and $AlCl_3.6H_2O$, 8.000 g of methanol, and 0.4000 g of bagasse are added into a reactor to form a mixture. The reactor is then sealed and heated to 190° C. with stirring to allow the mixture to react at 190° C. for a certain period of time (for reaction time, refer to Table 1). The reactor is cooled with water to room temperature, a certain quantity of n-butanol as an internal standard substance is added into the mixture, and the resulting mixture is well shaken and then taken into a centrifuge tube for centrifugal separation. Then, the supernatant is taken for gas chromatographic analysis. The yields of methyl lactate and methyl levulinate are shown in Table 1.

TABLE 1

Reactions at different reaction time with combination catalysts of $SnCl_2·2H_2O$ and $AlCl_3·6H_2O$

| Example | $SnCl_2·2H_2O/$ $AlCl_3·6H_2O/g$ | Reaction time/h | Yield of methyl lactate/% | Yield of methyl levulinate/% |
|---|---|---|---|---|
| Example 23 | 0.0681/0.2414 | 2 | 10.7 | 1.7 |
| Example 24 | 0.0669/0.2415 | 4 | 21.0 | 4.3 |
| Example 25 | 0.0678/0.2413 | 6 | 11.1 | 2.6 |
| Example 26 | 0.0678/0.2413 | 8 | 15.2 | 3.9 |
| Example 27 | 0.0680/0.2405 | 14 | 9.8 | 3.5 |

EXAMPLE 28

A combination catalyst of 0.2000 g of $SnCl_2.2H_2O$ and 0.1000 g of $ZnCl_2$, 8.000 g of methanol, and 0.4000 g of bagasse are added into a reactor to form a mixture. The reactor is then sealed and heated to 140° C. with stirring to allow the mixture to react at 140° C. for 4 h. The reactor is cooled with water to room temperature, a certain quantity of n-butanol as an internal standard substance is added into the mixture, and the resulting mixture is well shaken and then taken into a centrifuge tube for centrifugal separation. Then, the supernatant is taken for gas chromatographic analysis. The yield of methyl lactate is 4.7%, the yield of methyl levulinate is 0.3%, and the yield of methyl acetate is 3.1%.

EXAMPLE 29

A combination catalyst of 0.2000 g of $SnCl_2.2H_2O$ and 0.1189 g of $FeCl_3$, 8.000 g of methanol, and 0.4000 g of microcrystalline cellulose are added into a reactor to form a mixture. The reactor is then sealed and heated to 180° C. with stirring to allow the mixture to react at 180° C. for 4 h. The reactor is cooled with water to room temperature, a certain quantity of n-butanol as an internal standard substance is added into the mixture, and the resulting mixture is well shaken and then taken into a centrifuge tube for centrifugal separation. Then, the supernatant is taken for gas chromatographic analysis. The yield of methyl lactate is 11.8%, the yield of methyl levulinate is 4.3%, and the yield of methyl formate is 0.6%.

EXAMPLE 30

A combination catalyst of 0.2008 g of $SnCl_2.2H_2O$ and 0.1646 g of $ZnBr_2$, 8.000 g of methanol, and 0.4000 g of microcrystalline cellulose are added into a reactor to form a mixture. The reactor is then sealed and heated to 200° C. with stirring to allow the mixture to react at 200° C. for 4 h. The reactor is cooled with water to room temperature, a certain quantity of n-butanol as an internal standard substance is added into the mixture, and the resulting mixture is well shaken and then taken into a centrifuge tube for centrifugal separation. Then, the supernatant is taken for gas chromatographic analysis. The yield of methyl lactate is 23.2%, the yield of methyl levulinate is 16.6%, and the yield of methyl formate is 2%.

EXAMPLE 31

A combination catalyst of 0.2004 g of $SnCl_2.2H_2O$ and 0.1676 g of $SbCl_3$, 8.000 g of methanol, and 0.4000 g of microcrystalline cellulose are added into a reactor to form a mixture. The reactor is then sealed and heated to 190° C. with stirring to allow the mixture to react at 190° C. for 4 h. The reactor is cooled with water to room temperature, a certain quantity of n-butanol as an internal standard substance is added into the mixture, and the resulting mixture is well shaken and then taken into a centrifuge tube for centrifugal separation. Then, the supernatant is taken for gas chromatographic analysis. The yield of methyl lactate is 16.3%, the yield of methyl levulinate is 6.7%, and the yield of methyl formate is 1.2%.

EXAMPLE 32

A combination catalyst of 0.0687 g of $SbCl_3$ and 0.2660 g of $CrC_3.6H_2O$, 8.000 g of methanol, and 0.4000 g of bagasse are added into a reactor to form a mixture. The reactor is then sealed and heated to 190° C. with stirring to allow the mixture to react at 190° C. for 6 h. The reactor is cooled with water to room temperature, a certain quantity of n-butanol as an internal standard substance is added into the mixture, and the resulting mixture is well shaken and then taken into a centrifuge tube for centrifugal separation. Then, the supernatant is taken for gas chromatographic analysis. The yield of methyl lactate is 7.0%, and the yield of methyl levulinate is 8.1%.

EXAMPLE 33

A combination catalyst of 0.0689 g of $SbCl_3$ and 0.2415 g of $AlCl_3.6H_2O$, 8.000 g of methanol, and 0.4000 g of bagasse are added into a reactor to form a mixture. The reactor is then sealed and heated to 190° C. with stirring to allow the mixture to react at 190° C. for 6 h. The reactor is cooled with water to room temperature, a certain quantity of n-butanol as an internal standard substance is added into the mixture, and the resulting mixture is well shaken and then taken into a centrifuge tube for centrifugal separation. Then, the supernatant is taken for gas chromatographic analysis. The yield of methyl lactate is 8.8%, and the yield of methyl levulinate is 6.3%.

EXAMPLE 34

A combination catalyst of 0.0676 g of $SbCl_3$ and 0.1392 g of $ZnCl_2$, 8.000 g of methanol, and 0.4000 g of bagasse are added into a reactor to form a mixture. The reactor is then sealed and heated to 190° C. with stirring to allow the mixture to react at 190° C. for 6 h. The reactor is cooled with water to room temperature, a certain quantity of n-butanol as an internal standard substance is added into the mixture, and the resulting mixture is well shaken and then taken into a centrifuge tube for centrifugal separation. Then, the supernatant is taken for gas chromatographic analysis. The yield of methyl lactate is 11.6%, and the yield of methyl levulinate is 4.3%.

EXAMPLE 35

A combination catalyst of 1.0176 g of $SnCl_2.2H_2O$ and 0.4088 g of $ZnCl_2$, 60.0000 g of methanol, and 1.2008 g of cotton are added into a reactor to form a mixture. The reactor is then sealed and heated to 190° C. with stirring to allow the mixture to react at 190° C. for 7 h. The reactor is cooled with water to room temperature, a certain quantity of n-butanol as an internal standard substance is added into the reaction mixture, and the resulting mixture is well shaken and then taken into a centrifuge tube for centrifugal separation. Then, the supernatant is taken for gas chromatographic analysis. The yield of methyl lactate is 34.2%, the yield of methyl levulinate is 7.0%, the yield of methyl acetate is 0.6%, the yield of formaldehyde dimethyl acetal is 3.6%, and the yield of 2-methoxy acetaldehyde dimethyl acetal is 3.7%; and the residual solids are 0.5741 g.

EXAMPLE 36

A combination catalyst of 0.3389 g of $SnCl_2·2H_2O$ and 0.1365 g of $ZnCl_2$, 20.0 g of methanol, and 0.4002 g of the residual solid from the reaction in Example 35 are added into a reactor to form a mixture. The reactor is then sealed and heated to 190° C. with stirring to allow the mixture to react at 190° C. for 7 h. The reactor is cooled with water to room temperature, a certain quantity of n-butanol as an internal standard substance is added into the reaction mixture, and the resulting mixture is well shaken and then taken into a centrifuge tube for centrifugal separation. Then, the supernatant is taken for gas chromatographic analysis. The yield of methyl lactate is 9.5%, the yield of methyl formate is 0.2%, the yield of methyl levulinate is 4.4%, the yield of methyl acetate is 0.2%, the yield of formaldehyde dimethyl acetal is 0.5%, and the yield of 2-methoxy acetaldehyde dimethyl acetal is 0.3%; and the residual solids are 0.3468 g.

What is claimed is:

1. A catalyst for preparing lactic acid and derivatives thereof, comprising at least one of metallic compounds $MX_n$, wherein M is selected from Li, Na, K, Mg, Ca, Sr, Ba, Al, Ga, In, Sn, Sb, Bi, Cr, Mn, Fe, Co, Ni and Zn, n is an integer of 1 to 6; the anion X of the metallic compound $MX_n$ is selected from $F^-$, $Cl^-$, $Br^-$, $I^-$, $SO_4^{2-}$, $HSO_4^-$, $CH_3SO_3^-$, $C_6H_5SO_3^-$, $H_2PO_4^-$, $HPO_4^{2-}$, $PO_4^{3-}$, $PF_6^-$, $BO_2^-$, $BF_4^-$, $SiF_6^{2-}$ and $CH_3CO_2^-$; the catalyst comprise at least two of the metallic compounds $MX_n$, at least one of which is a metal halide.

2. The catalyst for preparing lactic acid and derivatives thereof of claim 1, wherein the metal ion in the metallic compound $MX_n$ is selected from $Li^+$, $Na^+$, $K^+$, $Mg^{2+}$, $Ca^{2+}$, $Sr^{2+}$, $Ba^{2+}$, $Al^{3+}$, $Ga^{3+}$, $In^{3+}$, $Sn^{2+}$, $Sn^{4+}$, $Sb^{3+}$, $Bi^{3+}$, $Cr^{3+}$, $Cr^{6+}$, $Mn^{2+}$, $Fe^{2+}$, $Fe^{3+}$, $Co^{2+}$, $Ni^{2+}$ and $Zn^{2+}$.

3. The catalyst for preparing lactic acid and derivatives thereof of claim 1, wherein the anion of the metallic compound $MX_n$ is selected from $F^-$, $Cl^-$, $Br^-$, $I^-$, $SO_4^{2-}$, $HSO_4^-$, $CH_3SO_3^-$, $C_6H_5SO_3^-$ and $CH_3CO_2^-$.

4. The catalyst for preparing lactic acid and derivatives thereof of claim 1, wherein the metal halide is a metal chloride.

5. The catalyst for preparing lactic acid and derivatives thereof of claim 4, wherein the metal chloride is $SnCl_2$, $SnCl_4$ or $SbCl_3$.

6. The catalyst for preparing lactic acid and derivatives thereof of claim 5, wherein the catalyst is selected from any one of combinations of $SnCl_2$ and $MgCl_2$, combinations of $SnCl_2$ and NaCl, combinations of $SnCl_2$ and $CaCl_2$, combinations of $SnCl_2$ and $AlCl_3$, combinations of $SnCl_2$ and $FeCl_3$, combinations of $SnCl_2$ and $SbCl_3$, combinations of $SnCl_2$ and $ZnCl_2$, and combinations of $SnCl_2$ and $ZnBr_2$.

7. The catalyst for preparing lactic acid and derivatives thereof of claim 5, wherein the catalyst is selected from any one of combinations of $SbCl_3$ and $CrCl_3$, combinations of $SbCl_3$ and NaCl, combinations of $SbCl_3$ and $CaCl_2$, combinations of $SbCl_3$ and $AlCl_3$, combinations of $SbCl_3$ and $FeCl_3$, combinations of $SbCl_3$ and $ZnCl_2$, and combinations of $SbCl_3$ and $ZnBr_2$.

8. A method for synthesis of lactic acid and derivatives thereof, comprising heating combinations of at least one raw material comprising carbohydrates, at least one alcohol, at least one catalyst and at least one solvent to make the combinations react, wherein the at least one catalyst is the catalyst of claim 1.

9. The method for synthesis of lactic acid and derivatives thereof of claim 8, wherein the raw material comprising carbohydrates is selected from at least one of monosaccharides and polysaccharides.

10. The method for synthesis of lactic acid and derivatives thereof of claim 9, wherein the raw material comprising carbohydrates is selected from at least one of starch, glucan, sucrose, fructose and glucose.

11. The method for synthesis of lactic acid and derivatives thereof of claim 8, wherein the raw material comprising carbohydrates is selected from at least one of lignocelluloses.

12. The method for synthesis of lactic acid and derivatives thereof of claim 11, wherein the raw material comprising carbohydrates is selected from at least one of cotton, bagasse, corn cob, cottonseed shell, wheat straw, rice straw, and microcrystalline cellulose.

13. The method for synthesis of lactic acid and derivatives thereof of claim 8, wherein the alcohol is selected from at least one of monohydric alcohols, dihydric alcohols and polyhydric alcohols.

14. The method for synthesis of lactic acid and derivatives thereof of claim 13, wherein the monohydric alcohol is selected from at least one of methanol, ethanol, 1-propanol, 2-propanol, 1-butanol, 2-butanol, and tert-butanol.

15. The method for synthesis of lactic acid and derivatives thereof of claim 13, wherein the dihydric alcohol is selected from at least one of ethylene glycol, 1,2-propylene glycol, and 1,3-propylene glycol.

16. The method for synthesis of lactic acid and derivatives thereof of claim 13, wherein the polyhydric alcohol is glycerol.

17. The method for synthesis of lactic acid and derivatives thereof of claim 8, wherein the solvent is a polar solvent which is selected from at least one of water, alcohols, and fatty acid methyl esters of C8-C22.

18. The method for synthesis of lactic acid and derivatives thereof of claim 17, wherein the solvent is selected from at least one of methanol, ethanol, 1-propanol, 2-propanol, 1-butanol, 2-butanol, tert-butanol, ethylene glycol, 1,2-propylene glycol, 1,3-propylene glycol, and glycerol.

19. The method for synthesis of lactic acid and derivatives thereof of claim 8, wherein a heating temperature is 80° C.-130° C.

20. The method for synthesis of lactic acid and derivatives thereof of claim 19, wherein the heating temperature is 120° C.-130° C.

21. The catalyst for preparing lactic acid and derivatives thereof of claim 1, wherein a heating temperature is 80° C.-130° C.

22. The catalyst for preparing lactic acid and derivatives thereof of claim 21, wherein the heating temperature is 120° C.-130° C.

* * * * *